US008932245B2

(12) United States Patent
Chen

(10) Patent No.: US 8,932,245 B2
(45) Date of Patent: Jan. 13, 2015

(54) VENTILATIVE ORTHOPEDIC BOOT WITH AN AIR CUSHION

(71) Applicant: Tung-Cheng Chen, Taichung (TW)

(72) Inventor: Tung-Cheng Chen, Taichung (TW)

(*) Notice: Subject to any disclaimer, the term of this patent is extended or adjusted under 35 U.S.C. 154(b) by 63 days.

(21) Appl. No.: 13/671,591

(22) Filed: Nov. 8, 2012

(65) Prior Publication Data

US 2014/0128789 A1 May 8, 2014

(51) Int. Cl.
A61F 13/00 (2006.01)
A61F 5/01 (2006.01)

(52) U.S. Cl.
CPC ............ A61F 5/0195 (2013.01); A61F 5/0111 (2013.01)
USPC ...................... 602/27; 602/5; 602/13; 602/23

(58) Field of Classification Search
CPC ... A61F 5/0123; A61F 5/0125; A61F 5/0111; A61F 5/0127; A61F 5/05816; A61F 13/00; A61F 13/066
USPC ............. 602/5, 13, 23, 27–29; D24/191–192; 36/110, 117
See application file for complete search history.

(56) References Cited

U.S. PATENT DOCUMENTS

| 5,250,021 A | * | 10/1993 | Chang ............................. 602/27 |
| 5,857,987 A | * | 1/1999 | Habermeyer .................... 602/23 |
| D500,855 S | * | 1/2005 | Pick et al. ..................... D24/192 |
| 2002/0128574 A1 | * | 9/2002 | Darby ............................ 602/23 |
| 2007/0282230 A1 | * | 12/2007 | Valderrabano et al. ........ 601/152 |
| 2008/0294082 A1 | | 11/2008 | Chang |
| 2009/0287128 A1 | | 11/2009 | Ingimundarson |
| 2010/0234782 A1 | | 9/2010 | Hu |
| 2013/0310721 A1 | * | 11/2013 | Hu et al. ......................... 602/13 |

* cited by examiner

Primary Examiner — Kim M Lewis
(74) Attorney, Agent, or Firm — Alan D. Kamrath; Kamrath IP Lawfirm, P.A.

(57) ABSTRACT

An orthopedic boot has a boot body, a front cover and at least one binding strap. The boot body has a foot support, a leg support, an air cushion and a toecap. The leg support has a free edge provided with multiple slits and multiple vents. The air cushion is mounted on the foot support. Accordingly, the orthopedic boot is ventilative and can provide comfort to a user.

11 Claims, 5 Drawing Sheets

VENTILATIVE ORTHOPEDIC BOOT WITH AN AIR CUSHION

BACKGROUND OF THE INVENTION

1. Field of the Invention

The present invention relates to an orthopedic boot and, more particularly, to an orthopedic boot that is ventilative and has an air cushion.

2. Description of Related Art

During a rehabilitating process, an orthopedic boot is usually used to hold a twisted ankle or broken leg at a fixed position. A conventional orthopedic boot substantially comprises a foot support and a leg support. The leg support is connected with the foot support to hold a leg of a user at a fixed angle relative to the foot.

However, the conventional orthopedic boot is not ventilative, and the leg support of the conventional orthopedic boot has a stiff edge and abuts against the calves of the user to cause discomfort to the user. In addition, the conventional orthopedic boot is made of hard rubber, so wearing the conventional orthopedic boot is uncomfortable.

To overcome the shortcomings, the present invention provides a ventilative orthopedic boot to mitigate or obviate the aforementioned problems.

SUMMARY OF THE INVENTION

The main objective of the invention is to provide an orthopedic boot that is ventilative and that has an air cushion to provide a comfortable effect to a user.

The orthopedic boot has a boot body, a front cover and at least one binding strap. The boot body has a foot support, a leg support, an air cushion and a toecap. The foot support has a sole panel and two side walls formed on and protruding from two side edges of the sole panel. The leg support is connected to the side walls of the foot support, extends upward from the sole panel and has a free edge, multiple slits and multiple vents. The free edge is opposite to the foot support. The slits are formed in the free edge of the leg support to make the free edge of the leg support expandable. The vents are defined through the leg support. The air cushion is mounted on the foot support. The toecap is mounted on a front end of the foot support. The front cover is mounted on the boot body to close gaps between edges of the side walls of the foot support and the leg support. The at least one binding strap is mounted between the boot body and the front cover to securely connect the front cover on the boot body.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
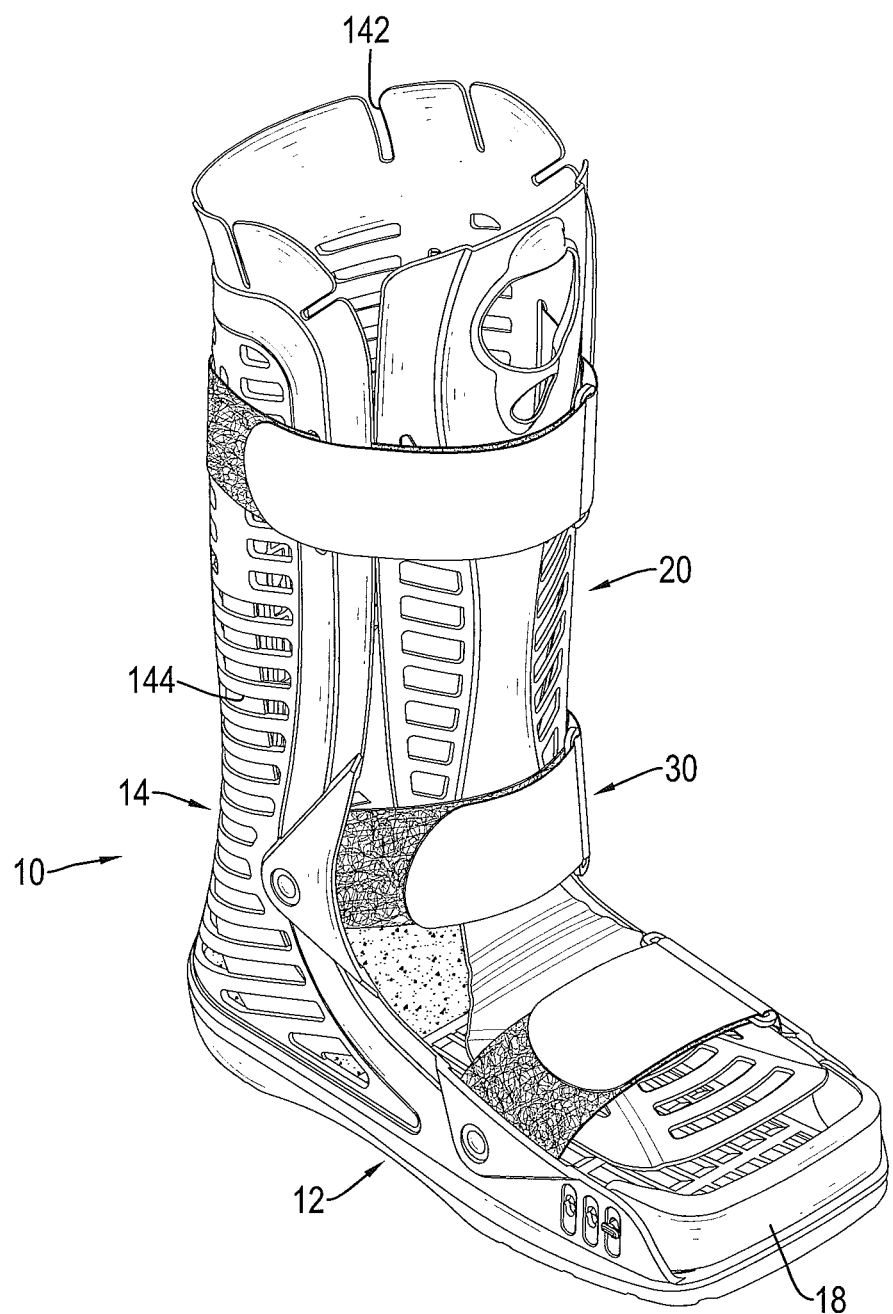
FIG. 1 is a perspective view of an orthopedic boot in accordance with the present invention.
Figure 2:
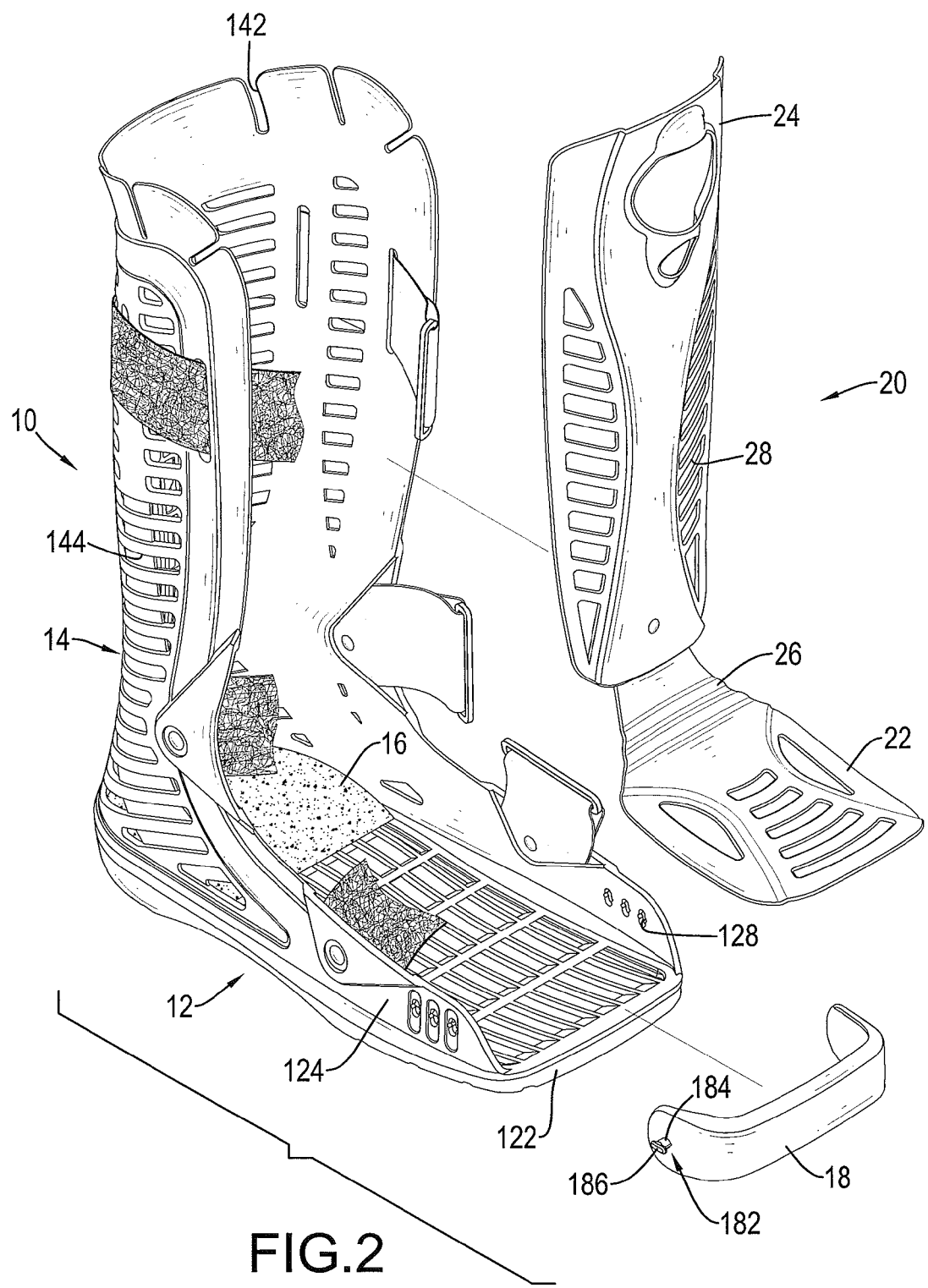
FIG. 2 is an exploded perspective view of the orthopedic boot in FIG. 1.
Figure 3:
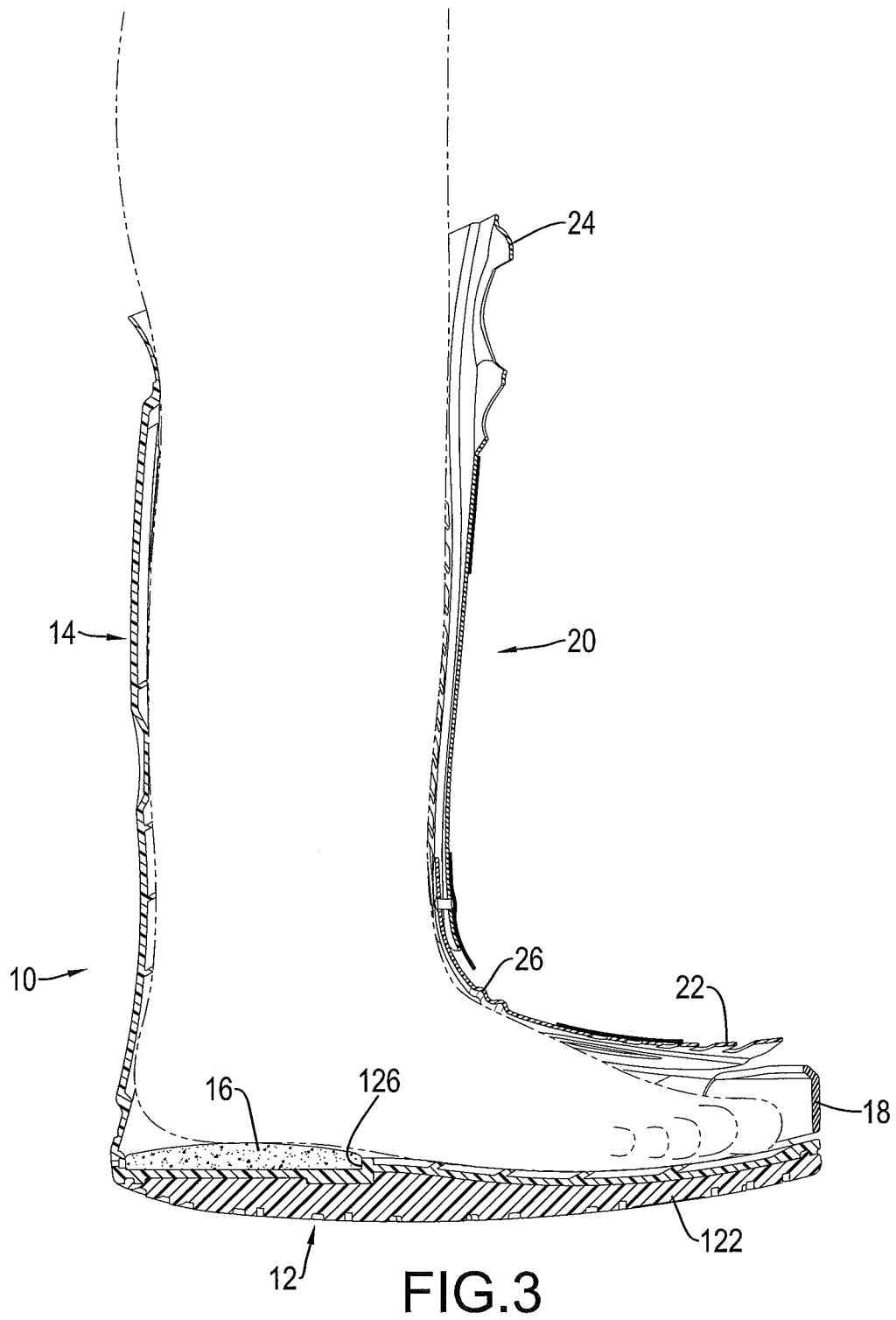
FIG. 3 is an operational side view in partial section of the orthopedic boot in FIG. 1.

With reference to FIGS. 1 to 3, an orthopedic boot in accordance with the present invention comprises a boot body 10, a front cover 20 and at least one binding strap 30. The boot body 10 has a foot support 12, a leg support 14, an air cushion 16 and a toecap 18.

The foot support 12 may have a U-shaped cross section and comprises a sole panel 122 and two side walls 124. The side walls 124 are respectively formed on and protrude from two side edges of the top of the sole panel 122. The leg support 14 may have a U-shaped cross section, is connected to the side walls 124 of the foot support 12, and extends upward from the sole panel 122. The leg support 14 has a free edge opposite to the foot support 12 and has multiple slits 142 formed in the free edge of the leg support 14 to make the free edge of the leg support 14 resilient and expandable. With the arrangement of the slits 142, the free edge of the leg support 14 can be expanded based on the shape of the calf of the user as shown in FIG. 3, such that the free edge of the leg support 14 can be kept from abutting against the calf of the user. Thus, wearing the orthopedic boot is comfortable. In addition, multiple vents 144 are formed through the leg support 14 to vent the orthopedic boot.

The air cushion 16 is mounted on the sole panel 122 and is preferable at a position corresponding to a heel of a user. To hold the air cushion 16 in position, a cushion recess 126 is defined in the top of the sole panel 122, and the air cushion 16 is mounted in the cushion recess 126. Alternatively, multiple air cushions 16 may be implemented and are mounted on the sole panel 122. With the arrangement of the air cushions 16, the foot of the user, especially to the ankle of the user, can be softly supported. The comfort of wearing the orthopedic boot can be enhanced.

Figure 4:
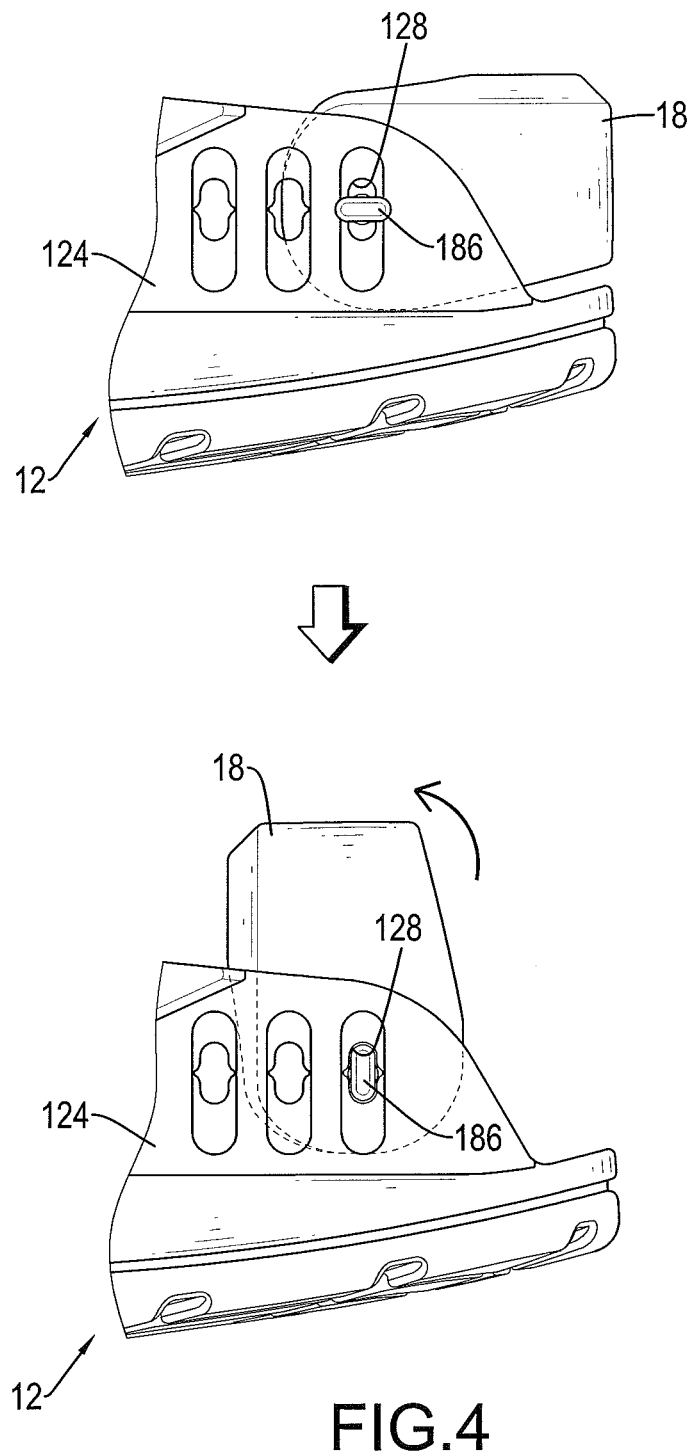
FIGS. 4 and 5 show enlarged operational side views of the orthopedic boot in FIG. 1 when the position of the toecap is changed.
Figure 5:
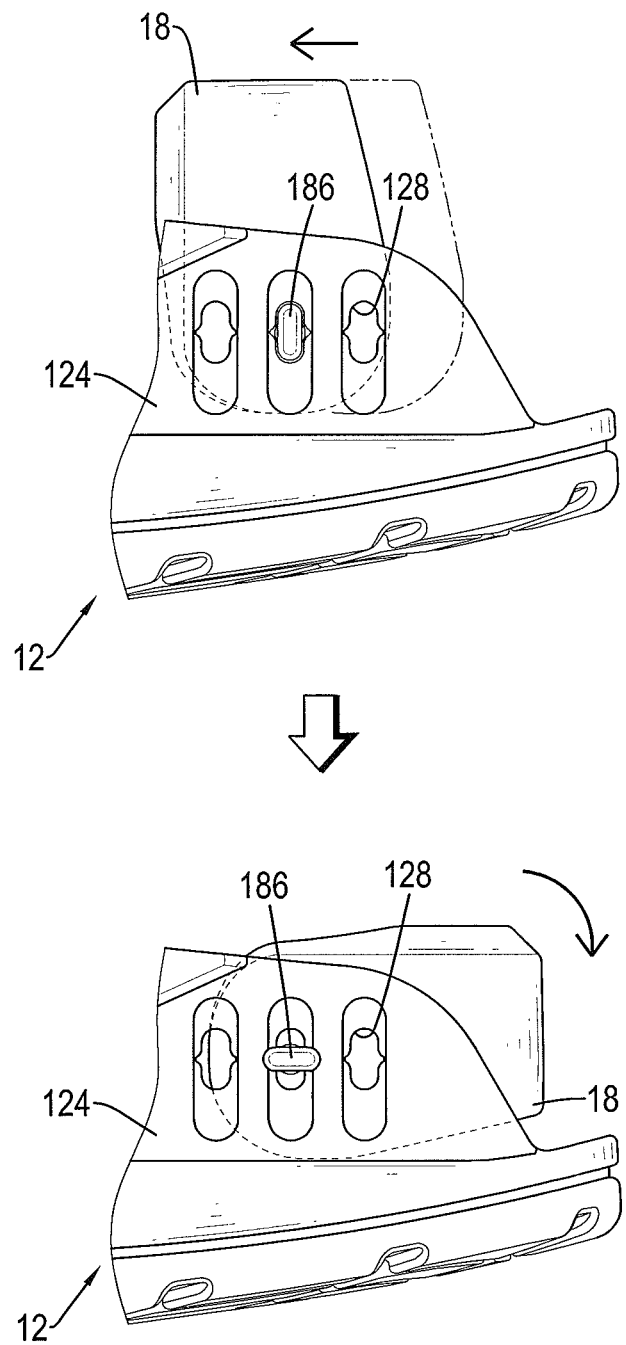

The toecap 18 is mounted on a front end of the foot support 12 and, preferably, is adjustably mounted on the front end of the foot support 12. The toecap 18 is U-shaped and has two ends and two connection shafts 182. The connection shafts 182 are formed respectively on the ends of the toecap 18, and each connection shaft 182 has a shaft body 184 and an enlarged head 186 formed on the shaft body 184. The foot support 12 has multiple connection holes 128 defined in the side walls 124 of the foot support 12 near the front end of the foot support 12 and arranged in multiple pairs. The connection holes 128 of each pair are formed respectively in the side walls 124 of the foot support 12 and align with each other. Each connection hole 128 is elongated and has a width and a height. The width of the connection holes 128 is larger than the diameter of the shaft bodies 184 of the connection shafts 182 and is smaller than the length of the enlarged heads 186 of the connection shafts 182. The height of the connection holes 128 is larger than the length of the enlarged heads 186 of the connection shafts 182. To connect the toecap 18 with the foot support 12, and with further reference to FIGS. 4 and 5, the enlarged heads 186 of the connection shafts 182 are respectively inserted through a pair of connection holes 128 along the length of the connection holes 128. The toecap 18 is then pivoted to make the enlarged heads 186 of the connection shafts 182 correspond to the width of the connection holes 128 in direction. Thus, the toecap 18 is connected to the side walls 124 of the foot support 12 and is not detached from the foot support 12. To change the position of the toecap 18, the toecap 18 is pivoted in reverse to make the enlarged heads 186 correspond to the length of the connection holes 128 in direction, such that the toecap 18 can be detached from the foot support 12 and can be connected with another pair of the connection holes 128. Accordingly, the position of the toecap 18 relative to the foot support 12 is adjustable to fit with different needs of different users.

With reference to FIGS. 1 to 3, the front cover 20 is attached to the boot body 10 to close gaps between edges of the side walls 124 of the foot support 12 and the leg support 14. The front cover 20 comprises a foot segment 22, a leg segment 24 and a conjunction segment 26. The foot segment 22 is attached to the top of the foot support 12 and closes the gap formed between edges of the side walls 124 of the foot support 12. The leg segment 24 is attached to the leg support 14 to close the gap between edges of the leg support 14. The conjunction segment 26 is formed between the foot segment 22 and the leg segment 24 and is resilient. As the conjunction segment 26 is resilient, the conjunction segment 26 will not block the foot of the user who wears the orthopedic boot, such that the user can walk freely and conveniently. In addition, multiple vents 28 are formed through the foot segment 22 and the leg segment 24 of the front cover 20 to enhance the ventilative effect of the orthopedic boot.

The at least one binding strap 30 is mounted between the boot body 10 and the front cover 20 to securely connect the front cover 20 on the boot body 10.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An orthopedic boot comprising:
   a boot body having:
   a foot support having:
   a sole panel;
   two side walls formed on and protruding from two side edges of the sole panel;
   a leg support connected to the two side walls of the foot support extending upward from the sole panel, and having:
   a free edge opposite to the foot support;
   multiple slits formed in the free edge of the leg support to make the free edge of the leg support expandable; and
   multiple vents defined through the leg support;
   an air cushion mounted on the foot; and
   a toecap mounted on a front end of the foot support and positioned in between the two side walls;
   a front cover mounted on the boot body to close gaps between edges of the two side walls of the foot support and the leg support; and
   at least one binding strap mounted between the boot body and the front cover to securely connect the front cover on the boot body, wherein:
   the foot support has multiple connection holes defined in the two side walls of the foot support near the front end of the foot support and arranged in multiple pairs; and
   the toecap has two connection shafts formed respectively on two ends of the toecap and connected to one of the multiple pairs of the multiple connection holes in the foot support.

2. The orthopedic boot as claimed in claim 1, wherein the air cushion is mounted on the sole panel at a position corresponding to a heel of a user.

3. The orthopedic boot as claimed in claim 2, wherein a cushion recess is defined in a top of the sole panel, and wherein the air cushion is mounted in the cushion recess.

4. The orthopedic boot as claimed in claim 3, wherein the toecap is adjustably mounted on the front end of the foot support and is U-shaped.

5. The orthopedic boot as claimed in claim 1, wherein:
   each connection shaft of the toecap has a shaft body and an enlarged head formed on the shaft body; and
   each connection hole in the foot support is elongated and has:
   a width being larger than a diameter of the shaft body of each connection shaft and smaller than a length of the enlarged head of each connection shaft; and
   a height being larger than the length of the enlarged head of each connection shaft.

6. The orthopedic boot as claimed in claim 5, wherein the front cover comprises:
   a foot segment attached to the top of the foot support to close a gap formed between edges of the two side walls of the foot support;
   a leg segment attached to the leg support to close a gap between edges of the leg support; and
   a conjunction segment being resilient and formed between the foot segment and the leg segment.

7. The orthopedic boot as claimed in claim 6, wherein the front cover further has multiple vents formed through the foot segment and the leg segment of the front cover.

8. The orthopedic boot as claimed in claim 1, wherein the toecap is adjustably mounted on the front end of the foot support and is U-shaped.

9. The orthopedic boot as claimed in claim 8, wherein:
   each connection shaft of the toecap has a shaft body and an enlarged head formed on the shaft body; and
   each connection hole in the foot support is elongated and has:
   a width being larger than a diameter of the shaft body of each connection shaft and smaller than a length of the enlarged head of each connection shaft; and
   a height being larger than the length of the enlarged head of each connection shaft.

10. The orthopedic boot as claimed in claim 1, wherein the front cover comprises:
    a foot segment attached to the top of the foot support to close a gap formed between edges of the two side walls of the foot support;
    a leg segment attached to the leg support to close a gap between edges of the leg support; and
    a conjunction segment being resilient and formed between the foot segment and the leg segment.

11. The orthopedic boot as claimed in claim 10, wherein the front cover further has multiple vents formed through the foot segment and the leg segment of the front cover.

* * * * *